US006579836B1

(12) United States Patent
Nevermann

(10) Patent No.: US 6,579,836 B1
(45) Date of Patent: Jun. 17, 2003

(54) AGENTS FOR ELIMINATING THE ADHESIVE CAPACITY OF HELMINTH EGGS

(75) Inventor: Jan Nevermann, Norderstedt (DE)

(73) Assignee: Menno Chemie Vertriebsges, mbH, Norderstedt (DE)

( * ) Notice: Subject to any disclaimer, the term of this patent is extended or adjusted under 35 U.S.C. 154(b) by 0 days.

(21) Appl. No.: 09/831,542

(22) PCT Filed: Sep. 13, 1999

(86) PCT No.: PCT/EP99/06768

§ 371 (c)(1), (2), (4) Date: Aug. 9, 2001

(87) PCT Pub. No.: WO00/27190

PCT Pub. Date: May 18, 2000

(30) Foreign Application Priority Data

Nov. 10, 1998 (DE) ........................................ 198 51 662

(51) Int. Cl.[7] ................................................ A61K 7/50

(52) U.S. Cl. ....................... 510/160; 510/275; 510/426; 510/477; 510/505; 510/506; 424/405

(58) Field of Search ................................ 510/160, 275, 510/426, 477, 505, 506; 424/405

(56) References Cited

FOREIGN PATENT DOCUMENTS

| | | | |
|---|---|---|---|
| CH | 513 969 | A | 11/1971 |
| DE | 196 43 585 | A | 4/1998 |
| EP | 0265 825 | A | 5/1988 |
| EP | 0338 398 | A | 10/1989 |
| EP | 0430 330 | A | 6/1991 |
| EP | 0875 239 | A | 11/1998 |

OTHER PUBLICATIONS

International Search Report for PCT/EP99/06768 (corresponding to present US application), 3 pages, dated Jan. 24, 2000.

*Primary Examiner*—Necholus Ogden

(57) ABSTRACT

The invention relates to detergents for removing adherent helminth eggs from the bristles, skin, fur and feathers of live animals. The detergents are based on an active mixture that can contain anion-active and/or non-ionic tensides, aromatic carboxylic acids, glycol ether, hydrotropic agents and oxygen donors and that is characterised in that it contains active combinations of aromatic carboxylic acids, preferably benzoic acid and o-hydroxybenzoic acid, individually or mixed, and/or their sodium, potassium or ammonium salts in conjunction with alkyl sulfonates or sulfates and/or alkylaryl sulfonates or sulfates with primary and/or secondary chains of the length $C_8$–$C_{18}$ and their sodium, potassium or ammonium salts as anionic tensides and alkylpolyethylene glycol ether $[R_nO\ (CH_2CH_2O)_xH;\ n=C_2–C_{10};\ x=3, 5, 6, 7, 8, 11]$ as non-ionogenic tensides, in that they contain triethylene glycol dimethylether, tetraethylene glycoldimethylether and n-hexyldiglycol (diethylene glycol-mono-n-hexylether) individually or mixed with each other, in that they contain toluol sulfonate and/or cumol sulfonate in the form of a sodium or a potassium salt as a solutizer, individually or mixed, and in that they contain potassium peroximonosulfate (triple salt), hydrogen peroxide, perborate or percarbonate and their sodium or potassium salts as oxygen donors.

13 Claims, No Drawings

AGENTS FOR ELIMINATING THE ADHESIVE CAPACITY OF HELMINTH EGGS

An infestation by parasites constitutes a great danger in agricultural stock keeping for breeding operations. Various types of helminths endanger different types of animals such as cattle, horses, swine, sheep and poultry. The endangering of livestock is independent of the type of keeping. Particular problems in the area of parasitoses by worms are presented in the following using the example of swine breeding. At the same time, these problems are suitable for illustrating the purpose of the present invention.

Of all the heimirth types, *Ascaris suum* (swine maw-worm) represents the most persistent potential of endangerment for swine stock. The cause for this is a so-called "direct development cycle" of this species.

The sexually mature Ascaris suum females deposit up to $10^6$ eggs per day in the intestine of the swine that are excreted with the excrement. The infectious larvae develop in the eggs within 6–8 weeks. If these eggs containing the larvae are ingested by the swine (from the soil, wall, and skin of the adjacent animals), the larvae will hatch in the small intestine. The larvae penetrate the intestinal wall, bore through the liver and pass via the blood to the lungs. After having broken through the lung tissue, the larvae are located in the air passageways of the lungs. The larvae are swallowed with the coughed-up mucous, pass into the small intestine and become adult worms. Bleeding and swellings of the swine liver are produced as a reaction to the migration of the larvae (cause of the "milk spots") and at the same time there is a significant interference with the metabolic efficiency. During the inspection of the meat, the liver is rejected given the presence of milk spots since it can no longer be used as foodstuff.

The cycle of infection can be interrupted in breeding operations for a brief time by the administration of anthelmintics [vermifuges] on the one hand and on the other hand by the use of special disinfection agents with ascaricidic action.

The anthelmintics administered usually effect only a reliable killing of the adult forms (worms and larvae) in the body of the animal and the disinfection agents kill off the maw-worm eggs on stall bottoms, walls and other surfaces in contact with the animals.

However, the cycle of excretion and re-infection begins again after only a brief time.

This is on account of the extremely adhesive surface, due to evolution, of the worm eggs that as a consequence adhere very firmly to the bristles, skin, teats and claws of the animals. The enormous adhesive capacity of the eggs is characteristic for very different helminth types. It is assumed that the ability to adhere to surfaces is the epidemiologically most significant method of propagation of maw-worm types.

The newly-born piglets become re-infected by licking each other and searching for the teats and the cycle of development starts anew.

Thus, the skin and bristles of contaminated animals are part of the causative-agent reservoir and constitute an important segment of the viscous circle of excretion, contamination and re-infection.

According to the previous state of the art, no washing or disinfecting agent is known that would be suitable for either removing the adhesive helminth eggs from the skin of the animals or killing the eggs.

Sufficiently efficacious disinfecting agents cannot be used without danger on the animal on account of their composition. No cleaning agent [detergent] that transports the worm eggs onto the stall bottom by washing them off, where a disinfection would then be possible, is known.

It was surprisingly found that a combination of certain anionic and non-anionic surfactants in the presence of aromatic acids, glycol ethers and an oxygen donor causes the helminth eggs to completely lose their adhesive capacity in a very brief time period upon contact with these agents. The components of the agents are considered to be non-toxic or have a low toxicity so that no danger to the animals is present when they are used in the concentration intended for use. After the loss of their adhesive capacity the eggs can be removed by simply washing off the bristles, skin, coat and feathers with water, which can interrupt the last link in the chain of infection.

The present invention has as subject matter cleaning agents for external application on animals in order to free them from infectious, adhesively adhering helminth eggs in that the adhesive capacity of the eggs is eliminated [neutralized] by the agents.

EXAMPLES ILLUSTRATING THE INVENTION

| Example 1) | Parts by weight |
|---|---|
| Alkylsulfonate-Na (40%) | 15.00 |
| Alkylarylsulfonate-Na (50%) | 10.00 |
| Alkylpolyethylene glycol ether[s] (R = $C_4$–$C_8$; x = 5–7) | 8.00 |
| Toluene sulfonate-Na (40%) | 10.00 |
| Benzoic acid-Na | 7.50 |
| o-Hydroxybenzoic acid | 6.00 |
| Triethylene glycol dimethylether[s] | 12.50 |
| Hydrogen peroxide sol. (35%) | 31.00 |

Example 2

Two-Component Preparation

| Component 1 | |
|---|---|
| Sec.-alkylsulfonate-Na (50%) | 20.00 |
| Alkylpolyethylene glycol ether[s] (R = $C_4$–$C_8$; x = 5–7) | 20.00 |
| Toluene sulfonate-Na (40%) | 30.00 |
| Benzoic acid-Na | 12.00 |
| Tetraethylene glycol dimethylether[s] | 18.00 |
| Component 2) | |
| Potassium peroxomonosulfate (triple salt) (potassium caroate) | 100.00 |

Description of an experimental setup for checking the effectiveness

Obtention of the Eggs

The eggs of *Ascaris suum* were obtained from the distal sections (approx. 2 cm long) of both uterine tubes of adult female maw worms by brushing them out with forceps. In order to determine the degree of development a part of the eggs was placed on a microscope slide and examined under a microscope. Eggs were brushed out of uteruses with ripe eggs into a vessel filled with tap water. The egg suspension obtained was transferred via a sieve with 200 $\mu$m mesh width into a siliconized storage vessel and stored until use at +4° C. in a refrigerator.

Decontamination of Swine Skin

Swine skin was prepared in squares of 2×5 cm and dried on the surface. The contamination of the skin took place by 0.5 ml of an egg suspension in water (approx. 130,000 eggs/ml). The preparations were subsequently dried 3h at room temperature. Thereafter, parallel washing procedures were carried out in 40 ml liquid for each procedure with a 2% aqueous solution of active substance according to example 1) and, in comparison thereto, with water of a standardized hardness ((WSH) in which the prepared swine skins were immersed 5, 10, 20 and 40 times in fresh wash solutions each time. After flotation of the eggs with a saturated solution of common salt the concentration of the eggs was determined from each wash solution by double determination in a McMaster counting chamber. The evaluation took place by calculating the detachment rate in percent relative to the initial egg count.

TABLE 1

Test for the detachment of *Asc. suum* eggs from swine skin

| Wash liquid | Detachment rate (%) after n different wash steps n = 5 | n = 10 | n = 20 | n = 40 |
|---|---|---|---|---|
| Example 1) | | | | |
| 2% solution | 8 | 18 | 40 | 72 |
| Water (WSH) | 2 | 7 | 10 | 10 |

Adhesion of Eggs to Polystyrene 5 ml of a 2% aqueous solution according to example 2) (1% component 1)+1% component 2)) were pipetted to 5 ml of an egg suspension, mixed and incubated at room temperature. Water with standardized hardness (WSH) was used for the control. After passage of the exposure times of 3, 5, 15, 30 and 60 min. the batches were drawn up 5 times in a 5 ml polystyrene pipette and transferred into a new tube. The concentration of the eggs in the last tube was subsequently determined by double counting in a McMaster counting chamber after flotation in a saturated solution of NaCl. The evaluation took place by calculating the it percentage recovery of Asc. suum eggs in percent in comparison to the initial egg suspension. The eggs remaining in the suspension (percentage recovery) are a direct measure of the capacity for preventing the adhesion to polystyrene surfaces, since it is known that helminth eggs have a high affinity for the latter.

TABLE 2

Test for the adhesion of *Ascaris suum* eggs to polystyrene

| Suspension medium of eggs | Percentage recovery (%) after different Exposure times (min.) 1 | 3 | 5 | 15 | 30 | 60 |
|---|---|---|---|---|---|---|
| Example 2) 2% | 100 | 99 | 98 | 100 | 100 | 100 |
| Water (WSH) | 63 | 13 | 8 | 3 | 2 | 1 |

What is claimed is:

1. A cleaning composition for removing adhering helminth eggs from the bristles, skin, coat and feathers of live animals, comprising a) at least one anion-active and/or non-ionogenic surfactant, wherein the anion-active surfactant is selected from the group consisting of alkyl sulfonates, alkyl sulfates, alkylaryl sulfonates, alkylaryl sulfates with primary and/or secondary chains having a length of $C_8$–$C_{18}$, and their sodium-, potassium- and ammonium salts, and wherein the non-ionogenic surfactant is an alkylpolyethylene glycol ether having the formula $R_nO(CH_2CH_2O)_xH$, where n=$C_2$–$C_{10}$ and x=3, 5, 6, 7, 8, 11, b) at least one aromatic carboxylic acid selected from the group consisting of benzoic acid, o-hydroxybenzoic acid, their sodium-, potassium- or ammonium salts, and mixtures thereof, c) at least one glycol ether selected from the group consisting of triethylene glycol dimethylether[s], tetraethylene glycol dimethyl ether[s], n-hexyldiglycol (diethylene glycol-mono-n-hexylether[s]), and mixtures thereof, d) at least one hydrotropic agent selected from the group consisting of toluene sulfonates and/or cumene sulfonate, and mixtures thereof, and e) at least one oxygen donor selected from the group consisting of potassium peroxymonosulfate, hydrogen peroxide, perborate, percarbonate, and their sodium and potassium salts.

2. The cleaning composition of claim 1, wherein the at least one anion-active surfactant is and alkyl sulfonate, an alkylarylsulfate, and/or their salts, and the weight ratio of the anion-active surfactant to the at least on aromatic carboxylic acid is between 1:9 and 9:1, and the sum of the at least one anion-active surfactant is between 10 and 60% relative to the total weight of the composition.

3. The cleaning composition of claim 1, wherein the weight of the at least one glycol ether relative to the total weight of the cleaning-agent concentrate is between 10 and 50% by weight.

4. The cleaning composition of claim 1, wherein the weight ratio of the at least one hydrotropic agent is between 5 and 40% by weight relative to the total weight of the composition.

5. The cleaning composition of claim 1, wherein the weight ratio of the at least one oxygen donor is between 5 and 70% by weight relative to the total weight of the composition.

6. The cleaning composition of claim 1, which composition is a liquid or a two-component preparation having a liquid component and a powder component.

7. A method for removing adhering helminth eggs from the bristles, skin, coat and feathers of live animals, comprising the step of applying to the bristles, skin, coat and feathers of live animals a cleaning composition comprising f) at least one anion-active and/or non-ionogenic surfactant, wherein the anion-active surfactant is selected from the group consisting of alkyl sulfonates, alkyl sulfates, alkylaryl sulfonates, alkylaryl sulfates with primary and/or secondary chains having a length of $C_8$–$C_{18}$, and their sodium-, potassium- and ammonium salts, and wherein the non-ionogenic surfactant is an alkylpolyethylene glycol ether having the formula $R_nO(CH_2CH_2O)_xH$, where n=$C_2$–$C_{10}$ and x=3, 5, 6, 7, 8, 11, g) at least one aromatic carboxylic acid selected from the group consisting of benzoic acid, o-hydroxybenzoic acid, their sodium-, potassium- or ammonium salts, and mixtures thereof, h) at least one glycol ether selected from the group consisting of triethylene glycol dimethylether[s], tetraethylene glycol dimethyl ether[s], n-hexyldiglycol (diethylene glycol-mono-n-hexylether[s]), and mixtures thereof, i) at least one hydrotropic agent selected from the group consisting of toluene sulfonates and/or cumene sulfonate, and mixtures thereof, and j) at least one oxygen donor selected from the group consisting of potassium peroxymonosulfate, hydrogen peroxide, perborate, percarbonate, and their sodium and potassium salts.

8. The method of claim 7, wherein the at least one anion-active surfactant is and alkyl sulfonate, an alkylarylsulfate, and/or their salts, and the weight ratio of the anion-active surfactant to the at least on aromatic carboxylic acid is between 1:9 and 9:1, and the sum of the at least one anion-active surfactant is between 10 and 60% relative to the total weight of the composition.

9. The method of claim 7, wherein the weight of the at least one glycol ether relative to the total weight of the cleaning-agent concentrate is between 10 and 50% by weight.

10. The method of claim 7, wherein the weight ratio of the at least one hydrotropic agent is between 5 and 40% by weight relative to the total weight of the composition.

11. The method of claim 7, wherein the weight ratio of the at least one oxygen donor is between 5 and 70% by weight relative to the total weight of the composition.

12. The method of claim 7, which composition is a liquid or a two-component preparation having a liquid component and a powder component.

13. The method of claim 7, wherein the composition is applied in dilute aqueous solutions containing between 0.5 and 10% by weight of the composition.

* * * * *